United States Patent
Shibamoto

(10) Patent No.: US 11,796,521 B2
(45) Date of Patent: Oct. 24, 2023

(54) GAS ANALYZER AND METHOD OF DETECTING STATE OF GAS ANALYZER

(71) Applicant: SHIMADZU CORPORATION, Kyoto (JP)

(72) Inventor: Shigeaki Shibamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/495,160

(22) Filed: Oct. 6, 2021

(65) Prior Publication Data

US 2022/0170896 A1 Jun. 2, 2022

(30) Foreign Application Priority Data

Nov. 30, 2020 (JP) ................. 2020-198800

(51) Int. Cl.
*G01N 33/00* (2006.01)
*G01N 30/38* (2006.01)
*G01N 30/02* (2006.01)

(52) U.S. Cl.
CPC ....... *G01N 33/0006* (2013.01); *G01N 33/007* (2013.01); *G01N 33/0073* (2013.01); *G01N 2030/025* (2013.01); *G01N 2030/385* (2013.01)

(58) Field of Classification Search
CPC ..... G01N 2223/646; G01N 2223/6466; G01N 33/0006; G01N 33/0009; G01N 1/22; G01N 33/0021; G01N 33/0026; G01N 33/0027; G01N 33/0032; G01N 33/0067; G01N 33/007; G08B 21/00

See application file for complete search history.

(56) References Cited

U.S. PATENT DOCUMENTS 4,254,654 A * 3/1981 Clouser ................. G01N 30/62
73/23.4
9,717,298 B1 * 8/2017 Barrett, Jr. ........... A61B 5/4064

FOREIGN PATENT DOCUMENTS

| CN | 101451982 A | * | 6/2009 |
| CN | 104500030 A | | 4/2015 |
| CN | 111624280 A | | 9/2020 |
| JP | 2015-190875 A | | 11/2015 |

OTHER PUBLICATIONS

First Office Action dated Aug. 23, 2023 for corresponding patent application CN 202111284515.5.

* cited by examiner

*Primary Examiner* — Harshad R Patel
*Assistant Examiner* — Truong D Phan
(74) *Attorney, Agent, or Firm* — Muir Patent Law, PLLC

(57) ABSTRACT

A gas analyzer includes: a column that separates a component in a sample gas; a valve that switches, between a test sample gas and a standard sample gas, the sample gas to be supplied to the column; a valve that adjusts an introduction amount of the sample gas to be supplied to the column; a detector that detects, by gas chromatography, the component in the sample gas separated by the column; and a control device. The control device controls the valve to allow the introduction amount to be a predetermined amount, calculates a peak area value of a chromatogram obtained by the detector when the introduction amount is the predetermined amount, and calculates a correspondence between the introduction amount and the peak area value.

9 Claims, 7 Drawing Sheets

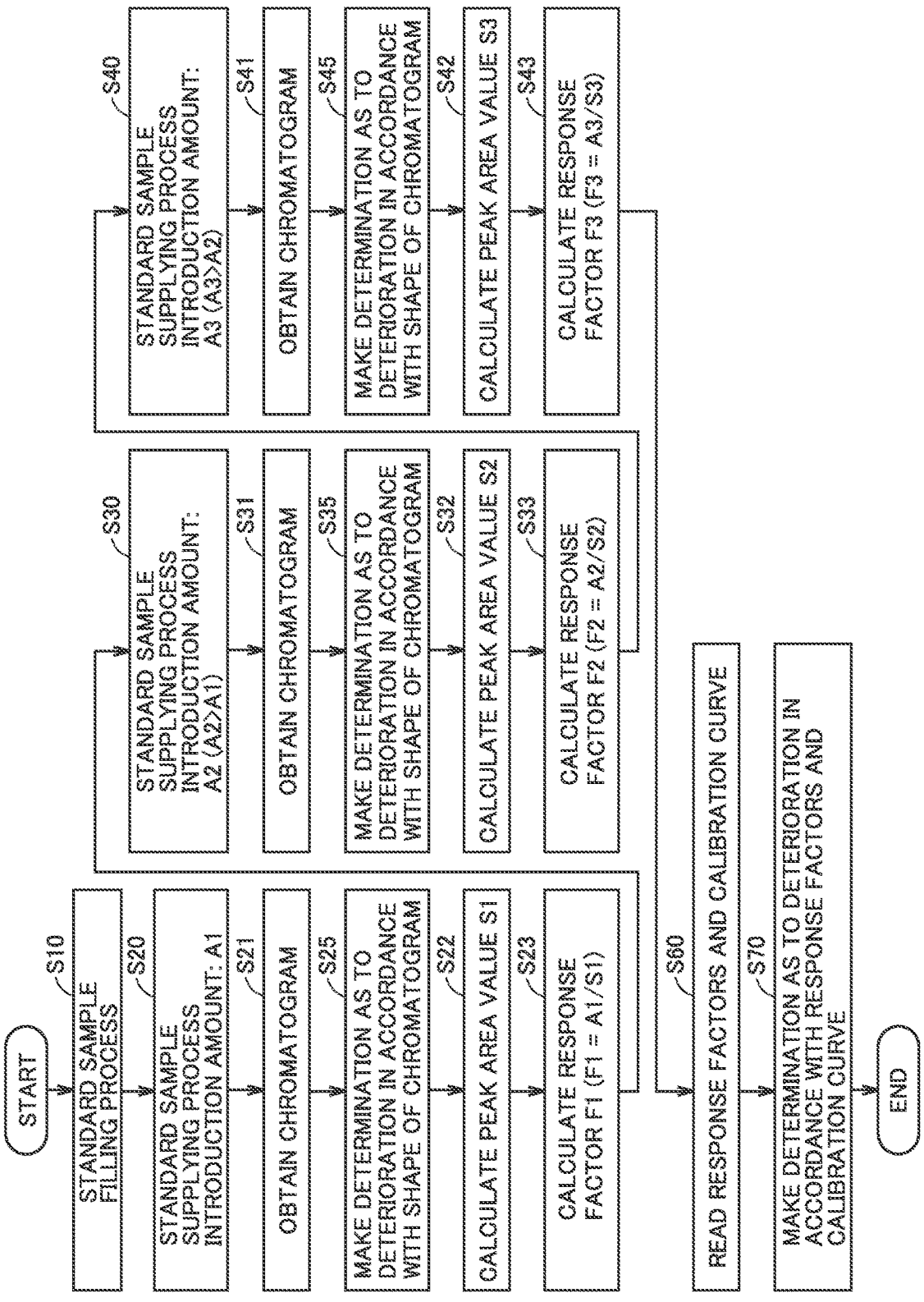

GAS ANALYZER AND METHOD OF DETECTING STATE OF GAS ANALYZER

BACKGROUND OF THE INVENTION

Field of the Invention

The present disclosure relates to a gas analyzer that detects a component in a sample gas by gas chromatography, and a method of detecting a state of the gas analyzer.

Description of the Background Art

Generally, a gas analyzer such as a gas chromatograph includes: a column that separates various components in a sample gas to be analyzed; a detector that detects, by gas chromatography, the components separated by the column; and the like. The sample gas is supplied to the column of the gas analyzer using a gas sampler. Normally, the gas sampler includes: a sample loop having a certain volume; a switching valve for switching a connection destination for the sample loop; and the like. By appropriately switching the connection destination for the sample loop by controlling the switching valve, the gas sampler temporarily fills the sample loop with the sample gas supplied from a sample gas source, and thereafter supplies a certain amount of the sample gas in the sample loop to the column of the gas analyzer (see Japanese Patent Laying-Open No. 2015-190875).

SUMMARY OF THE INVENTION

In such a gas analyzer, an analysis result may be deteriorated due to various causes such as deterioration of the column, contamination of the detector, adsorption/decomposition of a sample, and leakage of a small amount of gas. Therefore, it is general that a user who performs an analysis analyzes a standard sample gas and comprehensively identifies an abnormality in the gas analyzer in accordance with various analysis results such as reproducibility of repeated analyses and linearity of a calibration curve.

However, in order to identify an abnormality in the gas analyzer by the conventional method, it is necessary to prepare a plurality of containers filled with a plurality of standard sample gases having different concentrations, connect the containers to the gas analyzer, and sequentially switch between the concentrations of the standard sample gases to be supplied to the gas analyzer. Therefore, a special device is additionally required, thus resulting in a complicated overall configuration of the gas analyzer and increased cost or complicated user operation, disadvantageously. Japanese Patent Laying-Open No. 2015-81783 does not disclose such a problem and a countermeasure against the problem at all.

The present disclosure has been made to solve the above-described problem, and has an object to identify an abnormality in a gas analyzer using a simple configuration.

A gas analyzer according to an embodiment of the present disclosure includes: a column that separates a component in a sample gas; a switching valve that switches, between a test sample gas and a standard sample gas, the sample gas to be supplied to the column; an adjusting valve that adjusts an introduction amount of the sample gas to be supplied to the column; a detector that detects, by gas chromatography, the component in the sample gas separated by the column; and a control device that controls the switching valve and the adjusting valve. The control device controls the adjusting valve to allow the introduction amount to be a predetermined amount, calculates a peak area value of a chromatogram obtained by the detector with the adjusting valve being under the control, and calculates a correspondence between the introduction amount and the peak area value.

The gas analyzer includes: the switching valve that switches, between the test sample gas and the standard sample gas, the sample gas to be supplied to the column; and the adjusting valve that adjusts the introduction amount of the sample gas to be supplied to the column. Further, the control device controls the adjusting valve to allow the introduction amount to be the predetermined amount, calculates the peak area value when the introduction amount is the predetermined amount, and calculates the correspondence between the introduction amount and the peak area value. Therefore, for example, by controlling the switching valve to supply the standard sample gas to the column and by controlling the adjusting valve to allow the introduction amount to be predetermined various amounts, the correspondence between the introduction amount and the peak area value can be calculated for the predetermined various amounts. Thus, it can be determined whether or not the gas analyzer is deteriorated. On this occasion, the introduction amount of the sample gas to be supplied to the column can be controlled by the adjusting valve, so that it is not necessary to prepare a plurality of standard sample gases having different concentrations and it is also not necessary to additionally provide a special device for sequentially switching between the concentrations of the standard sample gases to be supplied to the gas analyzer. As a result, there can be provided a gas analyzer, by which an abnormality in the gas analyzer can be identified using a simple configuration.

A state detecting method according to an embodiment of the present disclosure is a method of detecting a state of a gas analyzer. The gas analyzer includes a column that separates a component in a sample gas. The state detecting method includes: supplying a predetermined amount of the sample gas to the column; calculating a peak area value of a chromatogram obtained with the predetermined amount of the sample gas being supplied to the column; and calculating a correspondence between an introduction amount of the sample gas and the peak area value.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a flowchart showing an exemplary process procedure performed when the control device makes a determination as to deterioration of the gas analyzer.

DESCRIPTION OF THE PREFERRED EMBODIMENTS

Figure 1:
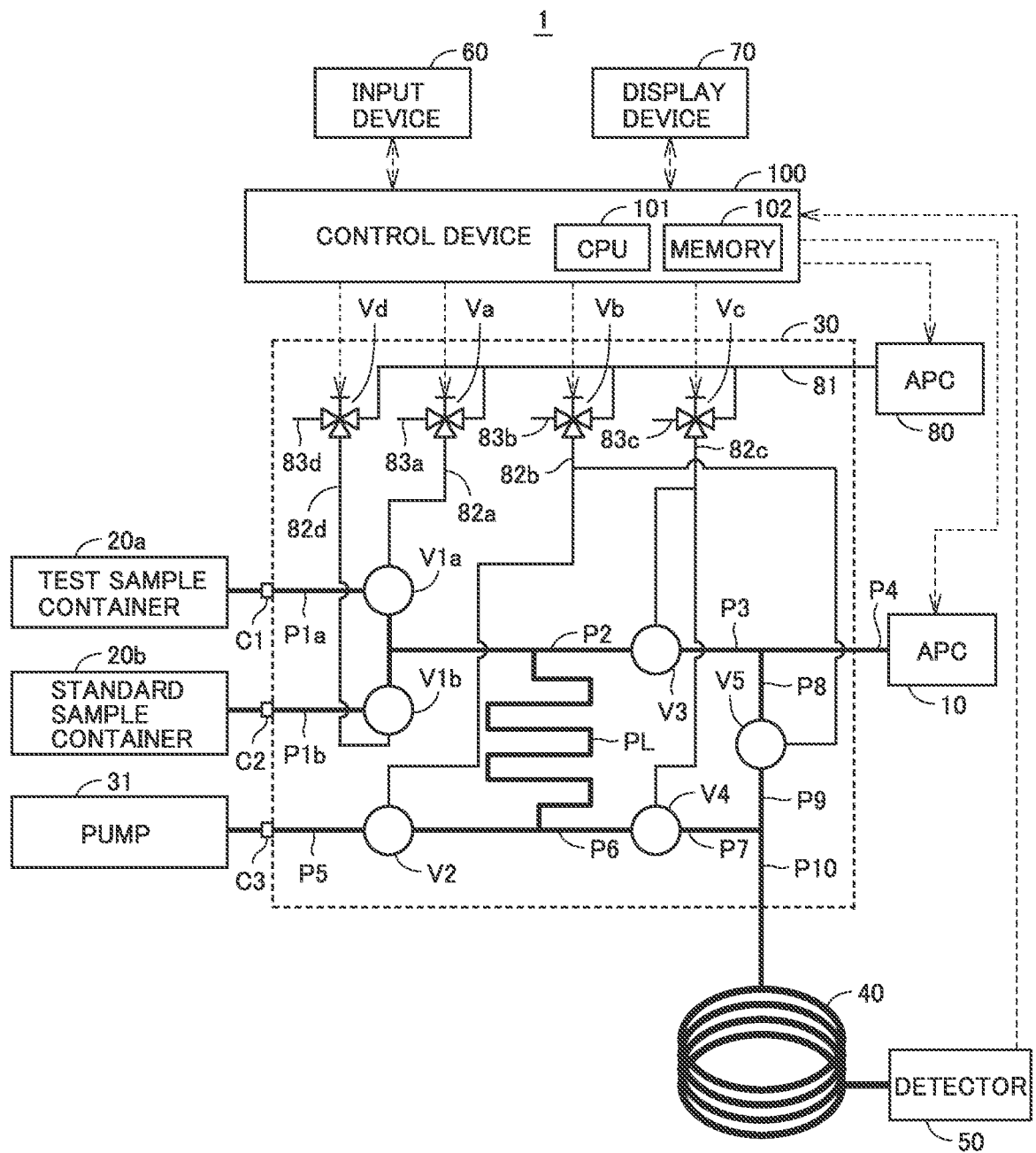
FIG. 1 is a diagram schematically showing an exemplary configuration of a gas analyzer (gas chromatograph).

Hereinafter, an embodiment of the present disclosure will be described in detail with reference to figures. It should be noted that in the figures, the same or corresponding portions are denoted by the same reference characters and will not be described repeatedly.

[Apparatus Configuration]

FIG. 1 is a diagram schematically showing an exemplary configuration of a gas analyzer (gas chromatograph) 1 according to the present embodiment.

Gas analyzer 1 includes electronic automatic pressure controllers (hereinafter, also referred to as "APC") 10, 80, a test sample container 20a, a standard sample container 20b, a gas sampler 30, a pump 31, a column 40, a detector 50, an input device 60, a display device 70, and a control device 100.

APC 10 adjusts a mobile phase, which is referred to as "carrier gas", to have a predetermined pressure and outputs it to a pipe P4. The carrier gas output from APC 10 to pipe P4 is supplied to column 40 through the inside of gas sampler 30. It should be noted that as the carrier gas, for example, a helium gas is used.

Test sample container 20a stores a test sample gas to be analyzed. Test sample container 20a is connected to a connection portion C1 of gas sampler 30. By replacing test sample container 20a connected to connection portion C1 of gas sampler 30, a user can change the test sample gas to be analyzed by gas analyzer 1.

Standard sample container 20b stores a standard sample gas having a known component. Standard sample container 20b is connected to a connection portion C2 of gas sampler 30. By replacing standard sample container 20b connected to connection portion C2 of gas sampler 30, the user can change the standard sample gas to be analyzed by gas analyzer 1.

Pump 31 is a suction pump for suctioning air in gas sampler 30 to attain a negative pressure in gas sampler 30. It should be noted that the term "negative pressure" herein means a pressure lower than the atmospheric pressure. Pump 31 is connected to a connection portion C3 of gas sampler 30.

Gas sampler 30 is a device for supplying the sample gas to column 40. Gas sampler 30 includes: connection portions C1, C2, C3; a sample loop PL having a certain volume; pipes P1a, P1b, P2 to P10; and valves V1a, V1b, V2 to V5. "Sample loop PL" in the present embodiment is an example of the "sample holding portion" in the present disclosure.

Connection portion C1 is connectable to test sample container 20a. Pipe P1a communicates connection portion C1 with valve V1a. Connection portion C2 is connectable to standard sample container 20b. Pipe P1b communicates connection portion C2 with valve V1b.

Pipe P2 communicates valves V1a, V1b with valve V3. Pipe P3 communicates valve V3 with pipe P4. Pipe P5 communicates pump 31 with valve V2. Pipe P6 communicates valve V2 with valve V4. Pipe P7 communicates valve V4 with pipe P10. Pipe P8 communicates pipe P4 with valve V5. Pipe P9 communicates valve V5 with pipe P10. Pipe P10 communicates pipe P9 with column 40. It should be noted that pipe P4 is branched into pipe P3 and pipe P8 in gas sampler 30. Pipe P7 and pipe P9 are merged into pipe P10 in gas sampler 30.

Sample loop PL is connected between pipe P2 and pipe P6. Sample loop PL has a function of temporarily holding the test sample gas introduced from test sample container 20a or the standard sample gas introduced from standard sample container 20b so as to supply it to column 40.

Each of valves V1a, V1b, V2 to V5 is a valve (so-called MEMS valve) having a very small dead volume and having been through micro-processing by a MEMS (Micro Electric Mechanical Systems) technique.

Further, each of valves V1a, V1b, V2 to V5 is a pneumatic valve that is opened and closed by driving air. Therefore, gas sampler 30 includes control valves Va to Vd, control pipes 81, 82a to 82d, and exhaust pipes 83a to 83d to control the driving air for valves V1a, V1b, V2 to V5. It should be noted that each of valves V1a, V1b, V2 to V5, each of which is a pneumatic MEMS valve, can respond at a higher speed than a rotary valve that switches a flow path by rotating a valve body, for example.

Each of valves V1a, V1b, V2 to V5 is a so-called normally open type valve that is in the opened state in an initial state in which no driving air is supplied and that is brought into the closed state when the driving air is supplied.

Valve V1a communicates with control valve Va via control pipe 82a, and is closed or opened in accordance with presence or absence of the driving air from control valve Va. Valve V1b communicates with control valve Vd via control pipe 82a, and is closed or opened in accordance with presence or absence of the driving air from control valve Vd. Each of valves V2, V5 communicates with control valve Vb via control pipe 82b, and is closed or opened in accordance with presence or absence of the driving air from control valve Vb. Each of valves V3, V4 communicates with control valve Vc via control pipe 82c, and is closed or opened in accordance with presence or absence of the driving air from control valve Vc.

APC 80 adjusts the driving air for controlling each of valves V1a, V1b, V2 to V5 to have a predetermined pressure and outputs it to control pipe 81. Each of control valves Va to Vd is a three-way electromagnetic valve that is controlled by an instruction signal from control device 100.

When control valve Va is controlled to communicate control pipe 81 and control pipe 82a with each other, valve V1a is supplied with the driving air and is therefore brought into the closed state. Accordingly, pipe P1a and test sample container 20a are disconnected from pipe P2. On the other hand, when control valve Va is controlled to communicate control pipe 82a and exhaust pipe 83a with each other, the driving air supplied to valve V1a is discharged to exhaust pipe 83a, so that valve V1a is brought into the opened state. Accordingly, pipe P1a and test sample container 20a communicate with pipe P2.

When control valve Vd is controlled to communicate control pipe 81 and control pipe 82a with each other, valve V1b is supplied with the driving air and is therefore brought into the closed state. Accordingly, pipe P1b and standard sample container 20b are disconnected from pipe P2. On the other hand, when control valve Vd is controlled to communicate control pipe 82d and exhaust pipe 83d with each other, the driving air supplied to valve V1b is discharged to exhaust pipe 83d, so that valve V1b is brought into the opened state. Accordingly, pipe P1b and standard sample container 20b communicate with pipe P2.

When control valve Vb is controlled to communicate control pipe 81 and control pipe 82b with each other, valves V2, V5 are supplied with the driving air and are therefore brought into the closed state. Accordingly, pipe P5 and pipe P6 are disconnected from each other and pipe P8 and pipe P9 are disconnected from each other. On the other hand, when control valve Vb is controlled to communicate control pipe 82b and exhaust pipe 83b with each other, the driving air supplied to valves V2, V5 is discharged to exhaust pipe 83b, so that valves V2, V5 are brought into the opened state. Accordingly, pipe P5 and pipe P6 communicate with each other and pipe P8 and pipe P9 communicate with each other.

When control valve Vc is controlled to communicate control pipe 81 and control pipe 82c with each other, valves V3, V4 are supplied with the driving air and are therefore brought into the closed state. Accordingly, pipe P2 and pipe P3 are disconnected from each other and pipe P6 and pipe P7 are disconnected from each other. On the other hand, when control valve Vc is controlled to communicate control pipe 82c and exhaust pipe 83c with each other, the driving air supplied to valves V3, V4 is discharged to exhaust pipe 83c, so that valves V3, V4 are brought into the opened state. Accordingly, pipe P2 and pipe P3 communicate with each other and pipe P6 and pipe P7 communicate with each other.

By appropriately switching the connection destination for sample loop PL by controlling valves V1a, V1b, V2 to V5, gas sampler 30 temporarily fills sample loop PL with the test sample gas supplied from test sample container 20a or with the standard sample gas supplied from standard sample container 20b, and then supplies the sample gas in sample loop PL to column 40. A method of supplying the sample gas to column 40 by gas sampler 30 will be described in detail later.

Column 40 separates various components in the sample gas (the test sample gas or the standard sample gas) supplied from gas sampler 30. Specifically, while the sample gas supplied to column 40 passes through column 40 due to flow of the carrier gas output from APC 10, the various components in the sample gas are separated at different times. The components separated in column 40 are introduced from column 40 to detector 50.

Detector 50 detects, by gas chromatography, each component in the sample gas separated in column 40. As detector 50, for example, a thermal conductivity detector (TCD), a flame ionization detector (FID), a flame photometric detector (FPD), a thermal ionization detector (TID), an electron capture detector (ECD), or a mass spectrometer is used. A detection result (hereinafter, also referred to as "chromatogram") by detector 50 is transmitted to control device 100 and is stored into control device 100. Further, the chromatogram stored in control device 100 is presented on display device 70 in response to a request from the user.

Input device 60 is a pointing device, such as a keyboard or a mouse, and receives an instruction from the user. Display device 70 is constituted of, for example, a liquid crystal display (LCD) panel, and presents information to the user. When a touch panel is used as a user interface, input device 60 and display device 70 are formed in one piece.

Control device 100 includes a CPU (Central Process Unit) 101, a memory 102, an interface (not shown), and the like. Control device 100 generally controls the whole of gas analyzer 1 including pump 31, APCs 10, 80, valves V1a, V1b, V2 to V5 (control valves Va to Vd), and the like. Control device 100 is wiredly or wirelessly connected to input device 60 and display device 70 each serving as the user interface.

When supplying the test sample gas from gas sampler 30 to column 40, control device 100 controls pump 31 and valves V1a, V1b, V2 to V5 to temporarily fill sample loop PL with the test sample gas supplied from test sample container 20, and thereafter supply column 40 with the test sample gas in sample loop PL.

When supplying the standard sample gas from gas sampler 30 to column 40, control device 100 controls pump 31 and valves V1a, V1b, V2 to V5 to temporarily fill sample loop PL with the standard sample gas supplied from standard sample container 20b, and thereafter supply column 40 with the standard sample gas in sample loop PL.

[Supply Operation of Sample Gas]

By performing below-described sample filling process and sample supplying process in this order, control device 100 temporarily fills sample loop PL with the sample gas and supplies column 40 with the sample gas in sample loop PL.

First, the sample filling process will be described. The sample filling process is a process of suctioning the sample gas into sample loop PL by using a negative pressure attained in sample loop PL using pump 31.

Figure 2:
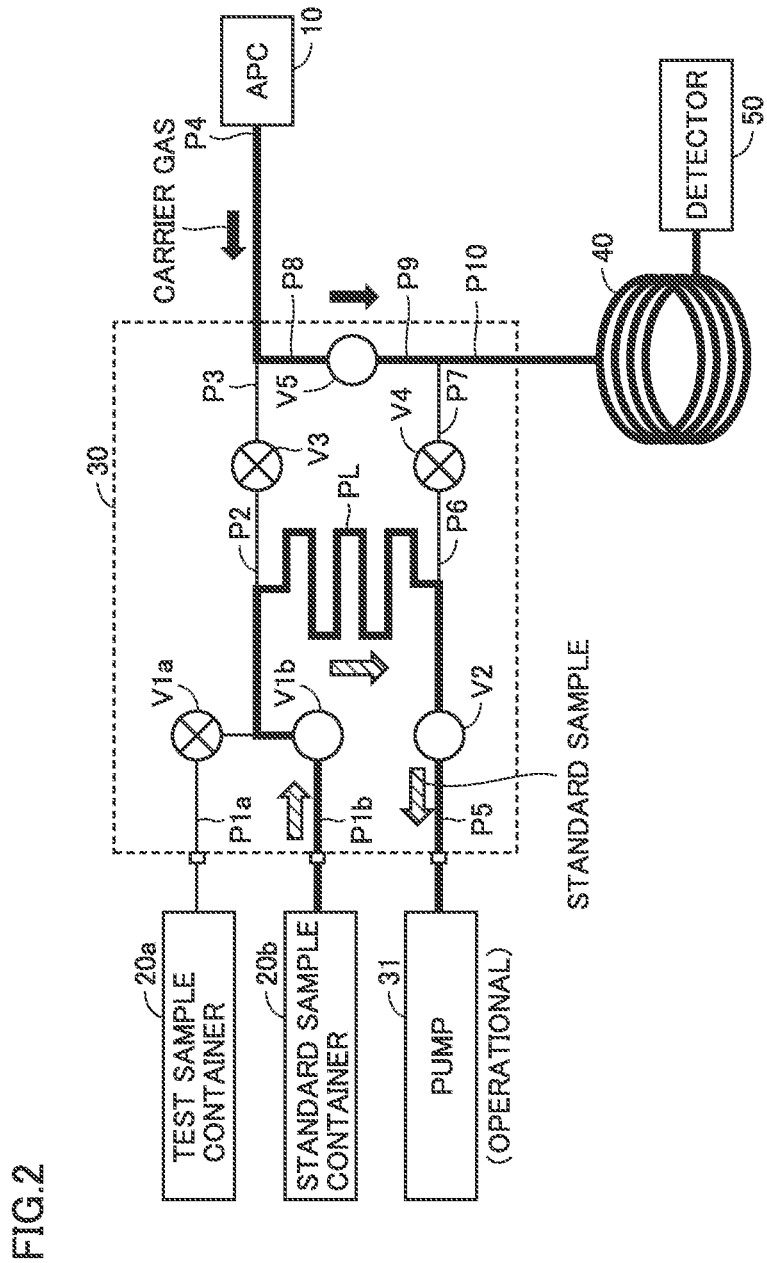
FIG. 2 is a diagram showing a state of a gas sampler during a sample filling process.

FIG. 2 is a diagram showing a state of gas sampler 30 during the sample filling process. It should be noted that FIG. 2 shows an example of filling sample loop PL with the standard sample gas as the sample gas.

During the sample filling process, control device 100 brings valves V1a, V3, V4 into the closed state and brings valves V1b, V2 into the opened state with pump 31 being operational. Accordingly, standard sample container 20b communicates with sample loop PL, with the result that sample loop PL is filled with the standard sample gas from standard sample container 20b by the operation of pump 31 as indicated by a shaded arrow. It should be noted that during the sample filling process, valve V5 is in the opened state and the carrier gas from APC 10 is supplied to column 40 as indicated by a solid arrow.

Although not shown in FIG. 2, when filling sample loop PL with the test sample gas in the sample filling process, valve V1a, rather than valve V1b, is brought into the opened state. Specifically, control device 100 brings valves V1b, V3, V4 into the closed state and brings valves V1a, V2 into the opened state with pump 31 being operational. Accordingly, test sample container 20a communicates with sample loop PL, thereby filling sample loop PL with the test sample gas from test sample container 20a. Each of "valves V1a, V1b" in the present embodiment is an example of the "switching valve" in the present disclosure.

Next, the sample supplying process will be described. The sample supplying process is a process of supplying, to column 40 by using the carrier gas, the sample gas provided in sample loop PL by the sample filling process.

Figure 3:
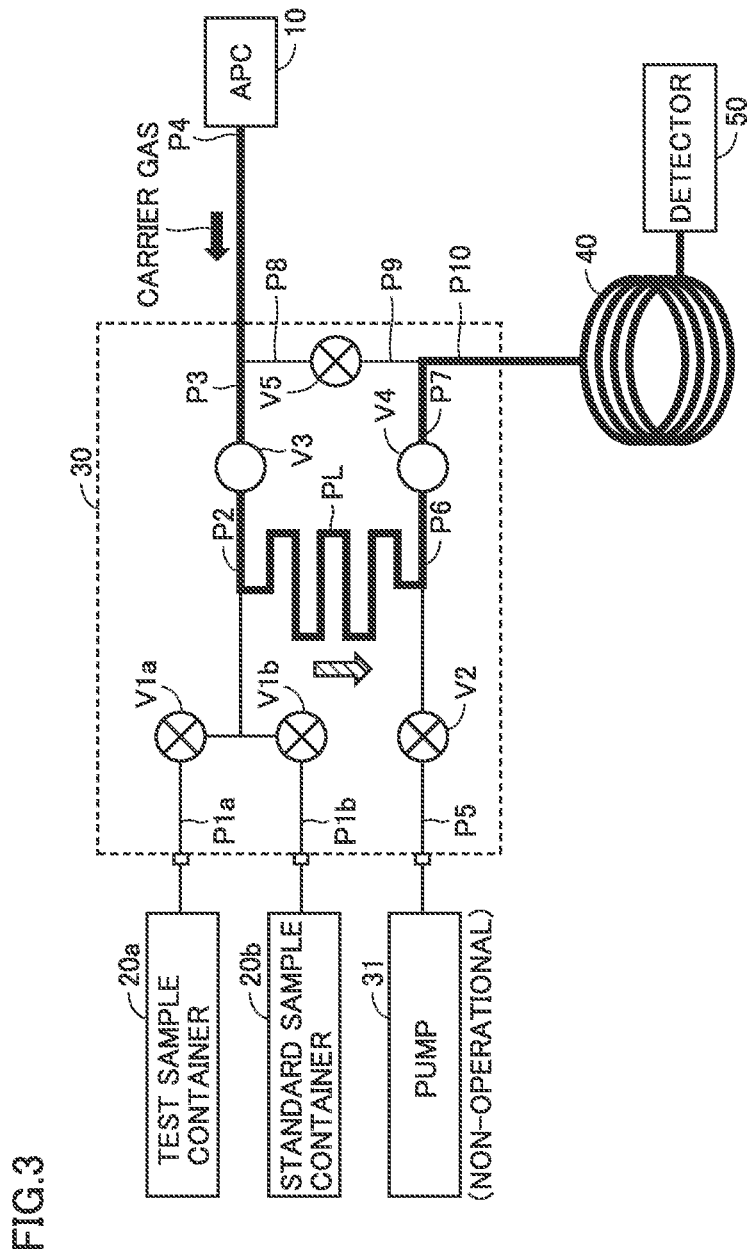
FIG. 3 is a diagram showing a state of the gas sampler during a sample supplying process.

FIG. 3 is a diagram showing a state of gas sampler 30 during the sample supplying process. During the sample supplying process, control device 100 brings valves V1a, V1b, V2, V5 into the closed state and brings valves V3, V4 into the opened state with pump 31 being non-operational. Thus, the carrier gas from APC 10 is supplied to sample loop PL through pipes P4, P3, P2, with the result that the standard sample gas in sample loop PL is pushed out by the carrier gas and is supplied to column 40 through pipes P6, P7, P10.

In the sample supplying process, control device 100 adjusts a time (hereinafter, also referred to as "open time") from the opening of valves V3, V4 to the closing of valves V3, V4, thereby adjusting an amount of the sample gas introduced into column 40 (hereinafter, also referred to as "gas introduction amount"). Each of "valves V3, V4" in the present embodiment is an example of the "adjusting valve" in the present disclosure.

[Creation of Calibration Curve and Determination as to Deterioration of Gas Analyzer]

It has been known that an analysis result by the gas analyzer may be deteriorated due to various causes such as deterioration of the column, contamination of the detector, adsorption/decomposition of the sample gas, and leakage of a small amount of gas. Therefore, conventionally, it is general that a user who performs an analysis analyzes a standard sample gas, examines linearity of a calibration curve, reproducibility of repeated analyses, and the like, and comprehensively determines whether or not the gas analyzer is deteriorated in accordance with the result of examination.

However, in order to create a calibration curve by the conventional method, it is necessary to prepare a plurality of standard sample containers filled with a plurality of standard sample gases having different concentrations, connect the standard sample containers to the gas analyzer, and sequentially switch between the concentrations of the standard sample gases to be supplied to the gas analyzer. Therefore, a special device is additionally required, thus resulting in a complicated overall configuration of the gas analyzer and increased cost, disadvantageously.

In view of the above point, gas analyzer 1 according to the present embodiment includes: valves V1a, V1b (switching valves) that each switch, between the test sample gas and the standard sample gas, the sample gas to be supplied to each of sample loop PL and column 40; and valves V3, V4 (adjusting valves) that each adjust the gas introduction amount of the sample gas to be supplied from sample loop PL to column 40. Therefore, by controlling valves V1a, V1b to switch, to the standard sample gas, the sample gas to be supplied to sample loop PL and column 40 and by controlling valves V3, V4 to stepwisely change the gas introduction amount of the sample gas to be supplied to column 40, a multipoint calibration curve can be created through the analysis of the standard sample gas and reproducibility of repeated analyses can be checked.

In particular, in the present embodiment, since MEMS valves each having a very small dead volume are used as valves V3, V4 (adjusting valves) that each adjust the gas introduction amount, the gas introduction amount can be precisely controlled by adjusting the open time (gas introduction time) of each of valves V3, V4.

Further, control device 100 according to the present embodiment controls valves V1a, V1b to switch, to the standard sample gas, the sample gas to be supplied to column 40 and controls valves V3, V4 to stepwisely change the gas introduction amount of the sample gas to be supplied to column 40, thereby automatically creating a multipoint calibration curve through the analysis of the standard sample gas.

Further, control device 100 according to the present embodiment calculates a correspondence (response factor F, which will be described later) between each gas introduction amount and a peak area value obtained from an analysis result for each gas introduction amount, and compares the calculated correspondence for each gas introduction amount, thereby determining whether or not gas analyzer 1 is deteriorated.

(Creation of Calibration Curve)

Figure 4:
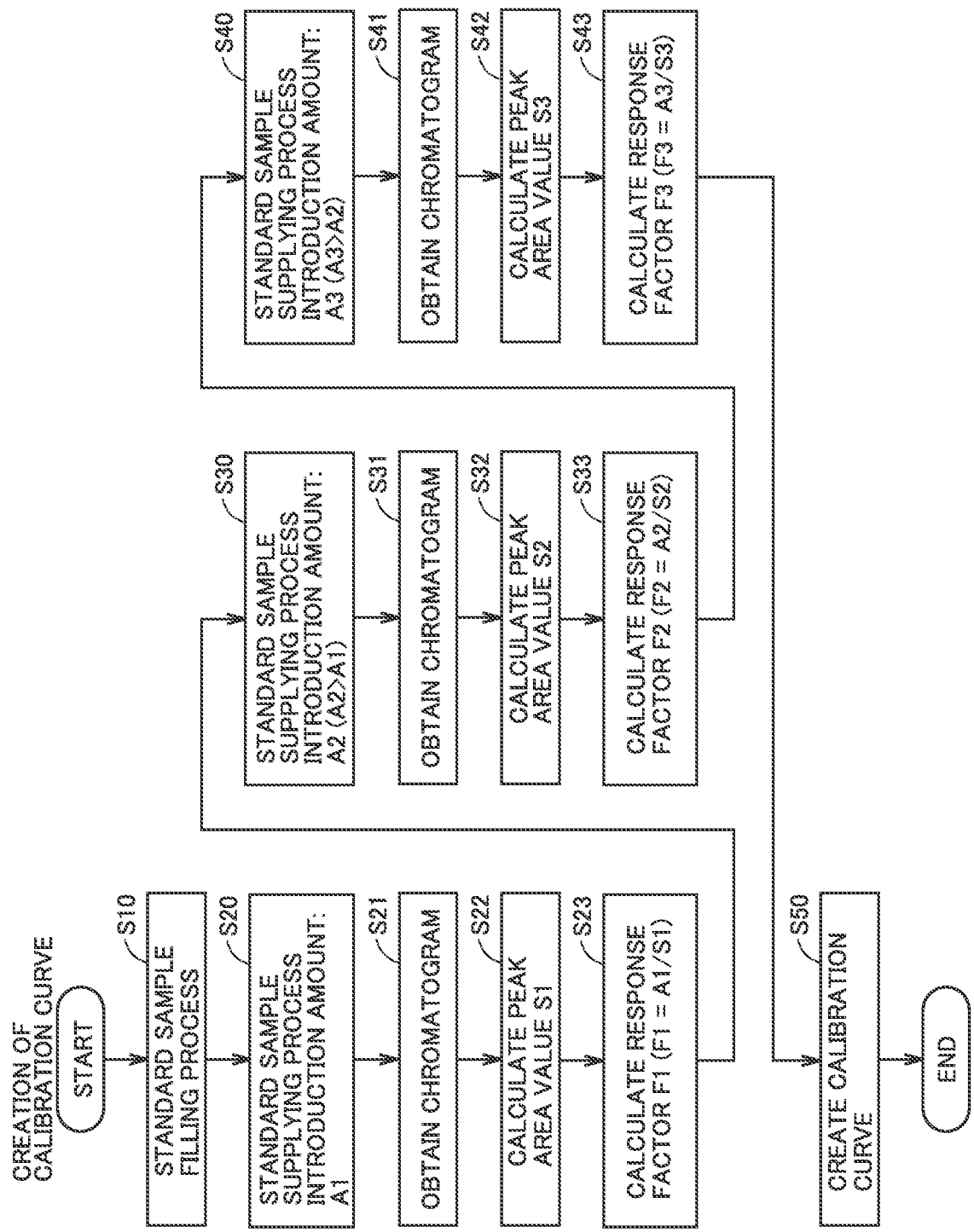
FIG. 4 is a flowchart showing an exemplary process procedure performed when a control device creates a calibration curve.

FIG. 4 is a flowchart showing an exemplary process procedure performed when control device 100 creates the calibration curve. The flowchart shown in FIG. 4 is performed, for example, when the user inputs, to input device 60, a manipulation for instructing creation of a calibration curve. The flowchart shown in FIG. 4 may be performed at the time of factory shipment of gas analyzer 1, for example.

First, control device 100 performs a process of filling sample loop PL with the standard sample gas (step S10). Specifically, as shown in FIG. 2, control device 100 brings valves V1a, V3, V4 into the closed state and brings valves V1b, V2 into the opened state with pump 31 being operational. Thus, sample loop PL is filled with the standard sample gas from standard sample container 20b.

Next, control device 100 performs a process of supplying, to column 40, a predetermined amount A1 of the standard sample gas in sample loop PL (step S20). Specifically, as shown in FIG. 3, control device 100 brings valves V1a, V1b, V2, V5 into the closed state and brings valves V3, V4 into the opened state with pump 31 being non-operational. Thus, the standard sample gas in sample loop PL is pushed out by the carrier gas and is supplied to column 40. On this occasion, control device 100 sets the open time of each of valves V3, V4 to a predetermined time T1, thereby allowing the introduction amount of the standard sample gas to be predetermined amount A1.

Next, from detector 50, control device 100 obtains a chromatogram obtained when the introduction amount of the standard sample gas is predetermined amount A1 (step S21).

Figure 5:
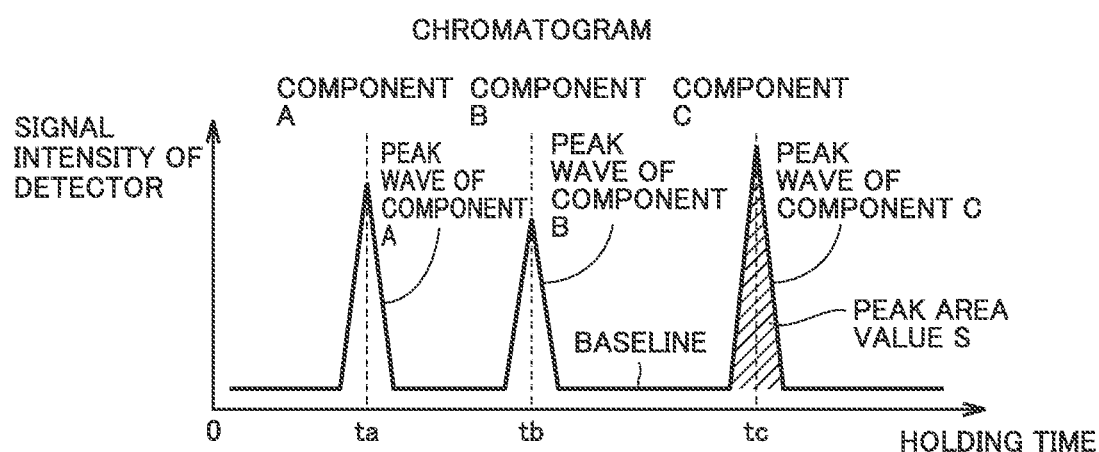
FIG. 5 is a diagram schematically showing a shape of a chromatogram.

FIG. 5 is a diagram schematically showing a shape of the chromatogram. In FIG. 5, the horizontal axis represents a holding time (a time from the introduction of the sample gas to appearance of a peak), and the vertical axis represents a signal intensity of detector 50. It should be noted that FIG. 5 illustrates a chromatogram obtained when a sample gas including components A, B, C is introduced into column 40 together with a carrier gas.

When the sample gas including components A, B, C is introduced into column 40 together with the carrier gas, the sample gas is moved in column 40 together with the carrier gas. A rate of movement in column 40 is varied depending on a component (compound) included in the sample gas. Therefore, the respective components reach the outlet of column 40 at different times, and due to an influence of this, peaks appear in the chromatogram at respective timings corresponding to the components.

Therefore, the holding time is a parameter indicating a component included in the sample gas. Further, the area of a portion surrounded by the baseline and a peak wave of the chromatogram (hereinafter also referred to as "peak area value") is a parameter indicating an amount of the component specified by the holding time. It should be noted that FIG. 5 shows an example in which the holding time of component A is "ta", the holding time of component B is "tb", and the holding time of component C is "tc".

In the description below, the following example will be described: the standard sample gas includes components A, B, C, and whenever the standard sample gas is introduced into column 40, the peak area value of component C at holding time tc (the area of the shaded portion shown in FIG. 5) is calculated as "peak area value S".

Referring back to FIG. 4, in accordance with the shape of the chromatogram obtained in step S21, control device 100 calculates, as a peak area value S1, peak area value S (the peak area value of component C at the holding time tc) obtained when the introduction amount of the standard sample gas is predetermined amount A1 (step S22).

Next, control device 100 calculates a response factor F1 obtained when the introduction amount of the standard sample gas is predetermined amount A1 (step S23). Response factor F1 is a value (=A1/S1) obtained by dividing predetermined amount A1 by peak area value S1. It should be noted that calculated response factor F1 is stored into memory 102.

Next, control device 100 performs the same processes as those in steps S20 to S23 with the introduction amount of the standard sample gas being changed to a predetermined amount A2 larger than predetermined amount A1 (steps S30 to S33). Specifically, control device 100 sets the open time of each of valves V3, V4 to a predetermined time T2 (T2>T1) so as to perform a process of supplying, to column 40, a predetermined amount A2 (A2>A1) of the standard sample gas in sample loop PL (step S30), and obtains a chromatogram in that case from detector 50 (step S31). Then, in accordance with the shape of the chromatogram obtained in step S31, control device 100 calculates a peak area value S2 obtained when the introduction amount of the standard sample gas is predetermined amount A2 (step S32), and calculates a response factor F2 (=A2/S2) obtained when the introduction amount of the standard sample gas is predetermined amount A2 (step S33). It should be noted that calculated response factor F2 is stored into memory 102.

Next, control device 100 performs the same processes as those in steps S20 to S23 with the introduction amount of the standard sample gas being changed to a predetermined amount A3 larger than predetermined amount A2 (steps S40 to S43). Specifically, control device 100 sets the open time of each of valves V3, V4 to a predetermined time T3 (T3>T2) so as to perform a process of supplying, to column 40, predetermined amount A3 (A3>A2) of the standard sample gas in sample loop PL (step S40), and obtains a chromatogram in that case from detector 50 (step S41). Then, in accordance with the shape of the chromatogram obtained in step S41, control device 100 calculates a peak area value S3 obtained when the introduction amount of the standard sample gas is predetermined amount A3 (step S42), and calculates a response factor F3 (=A3/S3) obtained when the introduction amount of the standard sample gas is predetermined amount A3 (step S43). It should be noted that calculated response factor F3 is stored into memory 102.

Next, control device 100 creates a multipoint calibration curve for component C in accordance with a relation between introduction amount A1 and peak area value S1, a relation between introduction amount A2 and peak area value S2, and a relation between introduction amount A3 and peak area value S3 (step S50).

Figure 6:
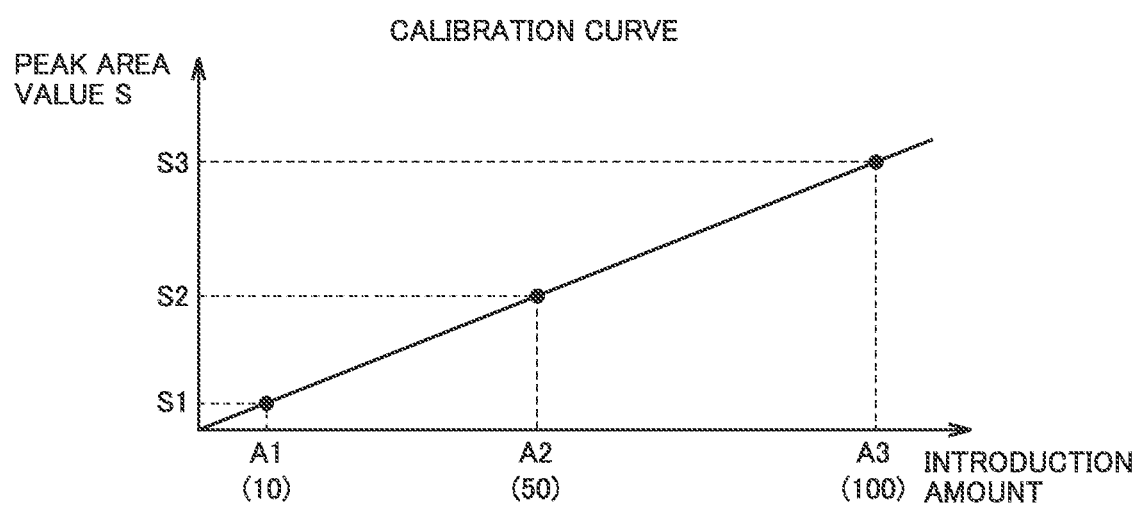
FIG. 6 is a diagram showing an exemplary calibration curve.

FIG. 6 is a diagram showing an exemplary calibration curve created in step S50. In the calibration curve shown in FIG. 6, the introduction amount of the standard sample gas is plotted in the horizontal axis, and peak area value S is plotted in the vertical axis. It should be noted that the calibration curve differs depending on each component. In the present embodiment, an example of creating a calibration curve for component C is illustrated. It should be noted that a calibration curve for component A or B may be created.

When analyses are performed under the same analysis condition, peak area value S of component C is proportional to the amount of the component. Therefore, the relation between introduction amount A1 and peak area value S1, the relation between introduction amount A2 and peak area value S2, and the relation between introduction amount A3 and peak area value S3 are all present on one proportional straight line passing through the origin, and response factors F1, F2, F3, each of which represents the slope thereof, have substantially the same value. Control device 100 creates such a calibration curve as shown in FIG. 6 in accordance with the relation between introduction amount A1 and peak area value S1, the relation between introduction amount A2 and peak area value S2, and the relation between introduction amount A3 and peak area value S3.

The calibration curve created in step S50 is stored in memory 102 of control device 100. It should be noted that by using the calibration curve, an amount of component C included in a test sample gas having unknown components can be detected.

(Determination as to Deterioration of Gas Analyzer)

FIG. 7 is a flowchart showing an exemplary process procedure performed when control device 100 makes a determination as to deterioration of gas analyzer 1. The flowchart shown in FIG. 7 is performed at a timing after the timing at which the calibration curve is created by the process of the flowchart shown in FIG. 4 (for example, after the time of factory shipment of gas analyzer 1) and is performed when the user inputs, to input device 60, a manipulation for instructing to make a determination as to deterioration of gas analyzer 1, for example.

The flowchart shown in FIG. 7 is obtained by removing step S50 from the flowchart shown in FIG. 4 and adding steps S25, S35, S45, S60, S70 to the flowchart shown in FIG. 4. The other steps in FIG. 7 (steps denoted by the same reference characters as those in FIG. 4) have already been described and therefore will not be repeatedly described here in detail.

Control device 100 performs the process of filling sample loop PL with the standard sample gas (step S10), performs the process of supplying predetermined amount A1 of the standard sample gas in sample loop PL to column 40 (step S20), and obtains a chromatogram in that case from detector 50 (step S21).

Then, control device 100 performs a process of making a determination as to deterioration of gas analyzer 1 in accordance with the shape of the chromatogram obtained in step S21 (step S25). For example, control device 100 calculates a symmetry coefficient, which is an index indicating a degree of symmetry of a peak, in accordance with the shape of the chromatogram, and when the symmetry coefficient indicates a deteriorated degree of symmetry of the peak, control device 100 can determine that there is deterioration of column 40 or deterioration resulting from adsorption of the sample due to contamination of each portion.

Also when the standard sample gas is set to predetermined amount A2, the determination as to deterioration is performed in the same manner as in step S25 (step S35). Further, also when the standard sample gas is set to predetermined amount A3, the determination as to deterioration is performed in the same manner as in step S25 (step S45).

It should be noted that generally, the deteriorated peak shape (mainly, tailing) resulting from the adsorption of the sample due to the contamination of each portion becomes more significant as the introduction amount of the sample gas is smaller. Therefore, by comparing the peak shapes in the cases of the plurality of introduction amounts (predetermined amounts A1, A2, A3), precision in the determination as to deterioration of gas analyzer 1 may be improved. For example, when the peak shape in the case of predetermined amount A3, i.e., a large introduction amount is not deteriorated but a tailing occurs in the peak shape in the case of predetermined amount A1, i.e., a small introduction amount, it may be determined that gas analyzer 1 is deteriorated by adsorption of the sample due to contamination of each portion.

After the process of step S43, control device 100 reads, from memory 102, response factors F1 to F3 and the calibration curve, each of which was calculated and created at a timing before the timing at which the current determination as to deterioration is performed (for example, at the timing at which the process of the flowchart of FIG. 4 is performed) and is stored in memory 102 (step S60).

Then, control device 100 performs a process of making a determination as to deterioration of gas analyzer 1 using: response factors F1, F2, F3 each calculated at the timing at which the current determination as to deterioration is performed; and response factors F1, F2, F3 and the calibration curve each read from memory 102 (step S70).

Control device 100 makes a determination as to deterioration of gas analyzer 1 by comparing response factors F1, F2, F3 each calculated at the timing at which the current determination as to deterioration is performed. For example, when response factor F1 is larger than the other response factors F2, F3 due to peak area value S1 being decreased in the case of predetermined amount A1, i.e., the small introduction amount, it is determined that column 40 or detector 50 is deteriorated due to contamination. This is because surface activity is increased at the contaminated portion to facilitate sample adsorption/decomposition. In such a case, an analysis of a test sample gas should not be performed and it can be determined that maintenance of gas analyzer 1 is necessary.

Further, control device 100 determines whether or not gas analyzer 1 is deteriorated, by comparing response factors F1, F2, F3 each calculated at the current timing with the calibration curve read from memory 102. For example, when a difference between at least one of response factors F1, F2, F3 each calculated at the current timing and the slope of the calibration curve read from memory 102 is more than a reference value, it can be determined that gas analyzer 1 is deteriorated due to some factor.

Further, control device 100 determines whether or not gas analyzer 1 is deteriorated, by comparing response factors F1, F2, F3 each calculated at the current timing with response factors F1, F2, F3 read from memory 102. For example, when a difference between a corresponding one of response factors F1, F2, F3 each calculated at the current timing and a corresponding one of response factors F1, F2, F3 read from memory 102 is more than a reference value, it can be determined that gas analyzer 1 is deteriorated due to some factor.

It should be noted that the state of gas analyzer 1 may be determined in a more detailed manner as follows: the shapes of the chromatographs up to the previous one are stored and the shape of the chromatograph obtained at the current timing is compared therewith.

As described above, when creating the calibration curve, control device 100 according to the present embodiment controls valves V1$a$, V1$b$ to supply the standard sample gas to column 40 and controls valves V3, V4 to change the introduction amount to each of predetermined amounts A1, A2, A3. Then, control device 100 creates the calibration curve by calculating the respective correspondences between introduction amounts A1, A2, A3 and peak area values S1, S2, S3. When determining whether or not gas analyzer 1 is deteriorated, control device 100 controls valves V1$a$, V1$b$ to supply the standard sample gas to column 40, and controls valves V3, V4 to change the introduction amount to each of predetermined amounts A1, A2, A3. Then, in order to determine whether or not gas analyzer 1 is deteriorated, control device 100 calculates respective response factors F for introduction amounts A1, A2, A3, and compares calculated response factors F1, F2, F3 with the previously created calibration curve or response factors F1, F2, F3, each response factor F indicating a correspondence between a corresponding introduction amount and a corresponding peak area value. When performing these processes, the introduction amount of the standard sample gas to be supplied to column 40 can be controlled by valves V3, V4, so that it is not necessary to prepare a plurality of standard sample gases having different concentrations and it is also not necessary to additionally provide a special device for sequentially switching between the concentrations of the standard sample gases to be supplied to column 40. As a result, an abnormality in gas analyzer 1 can be identified using such a simple configuration.

[Aspects]

It is understood by one having ordinary skill in the art that the embodiments described above are specific examples of the following aspects.

(Clause 1) A gas analyzer according to one aspect includes: a column that separates a component in a sample gas; a switching valve that switches, between a test sample gas and a standard sample gas, the sample gas to be supplied to the column; an adjusting valve that adjusts an introduction amount of the sample gas to be supplied to the column; a detector that detects, by gas chromatography, the component in the sample gas separated by the column; and a control device that controls the switching valve and the adjusting valve. The control device controls the adjusting valve to allow the introduction amount to be a predetermined amount, calculates a peak area value of a chromatogram obtained by the detector with the adjusting valve being under the control, and calculates a correspondence between the introduction amount and the peak area value.

The gas analyzer according to clause 1 includes: the switching valve that switches, between the test sample gas and the standard sample gas, the sample gas to be supplied to the column; and the adjusting valve that adjusts the introduction amount of the sample gas to be supplied to the column. Further, the control device controls the adjusting valve to allow the introduction amount to be the predetermined amount, calculates the peak area value obtained when the introduction amount is the predetermined amount, and calculates the correspondence between the introduction amount and the peak area value. Therefore, for example, by controlling the switching valve to supply the standard sample gas to the column and by controlling the adjusting valve to allow the introduction amount to be predetermined various amounts, the correspondence between the introduction amount and the peak area value can be calculated for the predetermined various amounts. Thus, it can be determined whether or not the gas analyzer is deteriorated. On this occasion, the introduction amount of the sample gas to be supplied to the column can be controlled by the adjusting valve, so that it is not necessary to prepare a plurality of standard sample gases having different concentrations and it is also not necessary to additionally provide a special device for sequentially switching between the concentrations of the standard sample gases to be supplied to the gas analyzer. As a result, there can be provided a gas analyzer, by which an abnormality in the gas analyzer can be identified using a simple configuration.

(Clause 2) In the gas analyzer according to clause 1, the control device controls the switching valve to employ the standard sample gas as the sample to be supplied to the column, the control device controls the adjusting valve to allow the introduction amount to be predetermined various amounts, the control device calculates the correspondence for each of the predetermined various amounts, and the control device creates a calibration curve using the correspondences calculated for the predetermined various amounts.

According to the gas analyzer according to clause 2, a multipoint calibration curve can be created in accordance with the plurality of correspondences between the introduction amounts of the standard sample gas and the peak area values.

(Clause 3) In the gas analyzer according to clause 2, the control device is operable to identify an abnormality in the gas analyzer by comparing the correspondence calculated at a first timing with the calibration curve created before the first timing (for example, at the time of factory shipment of the gas analyzer).

According to the gas analyzer according to clause 3, for example, when the correspondence calculated at the first timing is deviated from the calibration curve created before the first timing (for example, at the time of factory shipment of the gas analyzer), it can be determined that there is an abnormality (deterioration) in the gas analyzer.

(Clause 4) In the gas analyzer according to clause 2, the control device is operable to identify an abnormality in the gas analyzer by comparing the correspondence of the standard sample gas calculated at a first timing with the correspondence of the standard sample gas calculated before the first timing.

According to the gas analyzer according to clause 4, when the correspondence calculated at the first timing is changed from the correspondence created before the first timing (for example, at the time of factory shipment of the gas analyzer), it can be determined that there is an abnormality (deterioration) in the gas analyzer.

(Clause 5) In the gas analyzer according to any one of clauses 1 to 4, the gas analyzer further includes: a first connection portion connectable to a first container that stores the test sample gas; a second connection portion connectable to a second container that stores the standard sample gas; and a sample holding portion that holds the sample gas to be supplied to the column. The switching valve is a pneumatic valve provided among the sample holding portion, the first connection portion and the second connection portion. The adjusting valve is a pneumatic valve provided between the sample holding portion and the column.

According to the gas analyzer according to clause 5, by controlling the switching valve, the sample gas to be held in the sample holding portion can be switched between the test sample gas and the standard sample gas. Further, by controlling the adjusting valve, the introduction amount of the sample gas from the sample holding portion into the column can be adjusted. Further, since each of the switching valve and the adjusting valve is a pneumatic valve that can respond at a high speed, the switching of the sample gas to be supplied to the column and the adjustment of the amount of the sample gas to be supplied to the column can be performed precisely.

(Clause 6) A state detecting method according to one aspect is a method of detecting a state of a gas analyzer. The gas analyzer includes a column that separates a component in a sample gas. The state detecting method includes: supplying a predetermined amount of the sample gas to the column; calculating a peak area value of a chromatogram obtained with the predetermined amount of the sample gas being supplied to the column; and calculating a correspondence between an introduction amount of the sample gas and the peak area value.

In the state detecting method according to clause 6, the same function and effect as those of the gas analyzer according to clause 1 can be exhibited.

(Clause 7) The state detecting method according to clause 6 includes: supplying a standard sample gas to the column; allowing the introduction amount to be predetermined various amounts; calculating the correspondence for each of the predetermined various amounts; and creating a calibration curve using the correspondences calculated for the predetermined various amounts.

According to the state detecting method according to clause 7, the same function and effect as those in the gas analyzer according to clause 2 can be exhibited.

(Clause 8) The state detecting method according to clause 7 further includes identifying an abnormality in the gas analyzer by comparing the correspondence created at a first timing with the calibration curve calculated before the first timing.

According to the state detecting method according to clause 8, the same function and effect as those of the gas analyzer according to clause 3 can be exhibited.

(Clause 9) The state detecting method according to clause 7 further includes identifying an abnormality in the gas analyzer by comparing the correspondence of the standard sample gas calculated at a first timing with the correspondence of the standard sample gas calculated before the first timing.

According to the state detecting method according to clause 9, the same function and effect as those of the gas analyzer according to clause 4 can be exhibited.

Although the embodiments of the present invention have been described, the embodiments disclosed herein are illustrative and non-restrictive in any respect. The scope of the present invention is defined by the terms of the claims, and is intended to include any modifications within the scope and meaning equivalent to the terms of the claims.

What is claimed is:

1. A gas analyzer comprising:
   a column that separates a component in a sample gas;
   a switching valve that switches, between a test sample gas and a standard sample gas, the sample gas to be supplied to the column;
   an adjusting valve that adjusts an introduction amount of the sample gas to be supplied to the column;
   a detector that detects, by gas chromatography, the component in the sample gas separated by the column; and
   a control device that controls the switching valve and the adjusting valve, wherein
   the control device controls the adjusting valve to allow the introduction amount to be a predetermined amount,
   the control device calculates a peak area value of a chromatogram obtained by the detector with the adjusting valve being under the control, and
   the control device calculates a correspondence between the introduction amount and the peak area value.

2. The gas analyzer according to claim 1, wherein
   the control device controls the switching valve to supply the standard sample gas to the column,
   the control device controls the adjusting valve to allow the introduction amount to be predetermined various amounts,
   the control device calculates the correspondence for each of the predetermined various amounts, and
   the control device creates a calibration curve using the correspondences calculated for the predetermined various amounts.

3. The gas analyzer according to claim 2, wherein the control device is operable to compare the correspondence calculated at a first timing with the calibration curve created before the first timing.

4. The gas analyzer according to claim 2, wherein the control device is operable to compare the correspondence of the standard sample gas calculated at a first timing with the correspondence of the standard sample gas calculated before the first timing.

5. The gas analyzer according to claim 1, further comprising:
- a first connection portion connectable to a first container that stores the test sample gas;
- a second connection portion connectable to a second container that stores the standard sample gas; and
- a sample holding portion that holds the sample gas to be supplied to the column, wherein
- the switching valve is a pneumatic valve provided among the sample holding portion, the first connection portion and the second connection portion, and
- the adjusting valve is a pneumatic valve provided between the sample holding portion and the column.

6. A method of operating a gas analyzer, the gas analyzer including a column that separates a component in a sample gas, the method comprising:
- switching, via switching valves, between a first supply line of a test sample gas and a second supply line of standard sample gas;
- supplying as the sample gas, via adjusting valves, a predetermined amount of the test sample gas or the standard sample gas to the column;
- calculating, via a control device, a peak area value of a chromatogram obtained with the predetermined amount of the sample gas being supplied to the column; and
- calculating, via the control device, a correspondence between an introduction amount of the sample gas and the peak area value.

7. The method of operating the gas analyzer according to claim 6, further comprising:
- supplying the standard sample gas to the column;
- allowing the supplied amount to be predetermined various amounts;
- calculating the correspondence for each of the predetermined various amounts; and
- creating a calibration curve using the correspondences calculated for the predetermined various amounts.

8. The method of operating the gas analyzer according to claim 7, further comprising comparing the correspondence created at a first timing with the calibration curve calculated before the first timing.

9. The method of operating the gas analyzer according to claim 7, further comprising identifying an abnormality in the gas analyzer by comparing the correspondence of the standard sample gas calculated at a first timing with the correspondence of the standard sample gas calculated before the first timing.

* * * * *